United States Patent [19]

Nerli

[11] Patent Number: 4,998,880
[45] Date of Patent: * Mar. 12, 1991

[54] DENTAL SYRINGE SAFETY SHEATH APPARATUS

[76] Inventor: Robert Nerli, 15 ElQuanito Way, Burlingame, Calif. 94010

[*] Notice: The portion of the term of this patent subsequent to Aug. 22, 2006 has been disclaimed.

[21] Appl. No.: 373,507

[22] Filed: Jun. 30, 1989

Related U.S. Application Data

[63] Continuation-in-part of Ser. No. 118,170, Nov. 9, 1987, Pat. No. 4,859,182.

[51] Int. Cl.⁵ .............................................. A61C 17/02
[52] U.S. Cl. ........................................ 433/80; 433/116
[58] Field of Search ...................... 433/80, 84, 91, 96, 433/116; 604/73, 77, 247

[56] References Cited

U.S. PATENT DOCUMENTS

| | | | |
|---|---|---|---|
| 3,401,691 | 9/1968 | Beu | 433/80 |
| 3,593,423 | 7/1971 | Jones et al. | 433/80 |
| 3,794,091 | 2/1974 | Ersek et al. | 128/6 |
| 4,106,501 | 8/1978 | Ozbey et al. | 433/80 |
| 4,531,912 | 7/1985 | Schuss et al. | 433/80 |
| 4,810,194 | 3/1989 | Snedden | 433/91 |

FOREIGN PATENT DOCUMENTS

| | | | |
|---|---|---|---|
| 442599 | 4/1927 | Fed. Rep. of Germany | 604/247 |
| 726286 | 11/1966 | Italy | 433/80 |

Primary Examiner—Mancene Gene
Assistant Examiner—Michael Lynch
Attorney, Agent, or Firm—David L. Garrison

[57] ABSTRACT

The present invention comprises a sheath for protecting a dental syringe and for preventing residual cross-contamination between successive patients. Means are provided for preventing contaminants from being drawn back into the syringe after application has ceased.

14 Claims, 3 Drawing Sheets

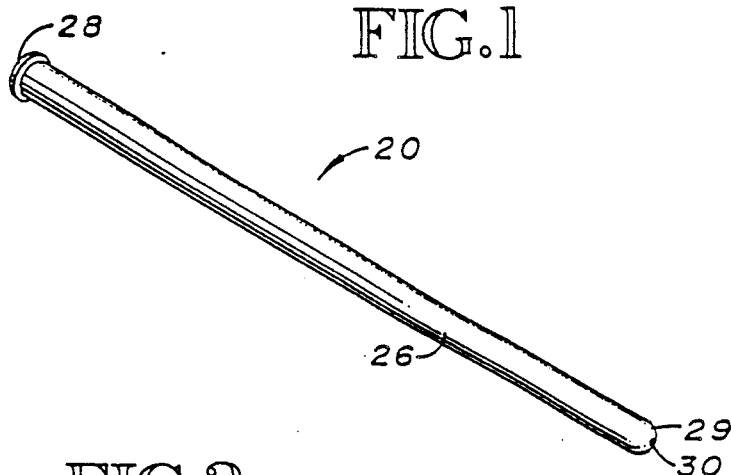
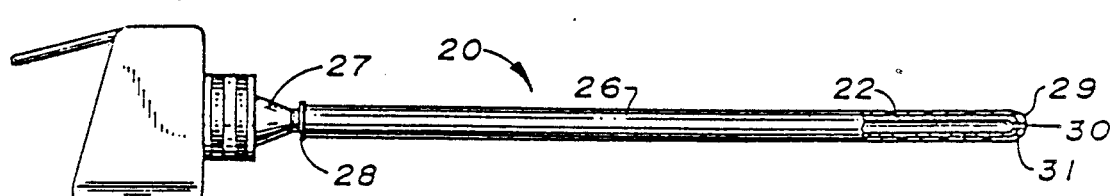
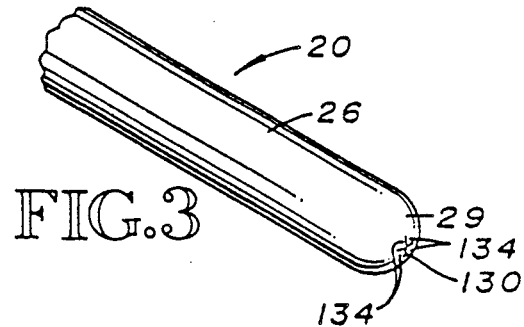
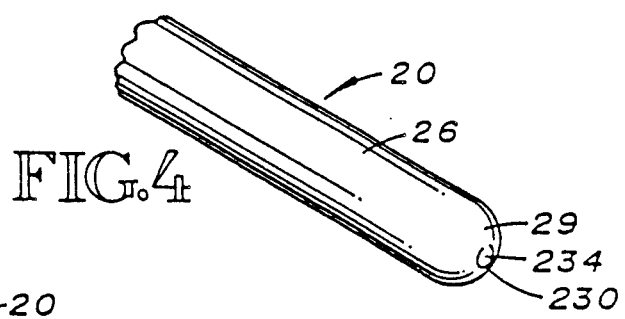
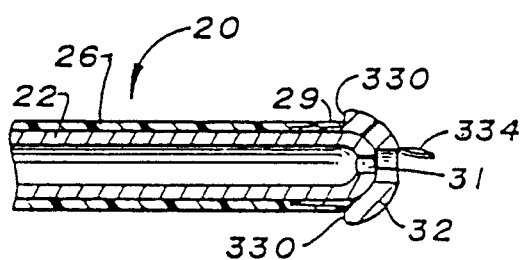

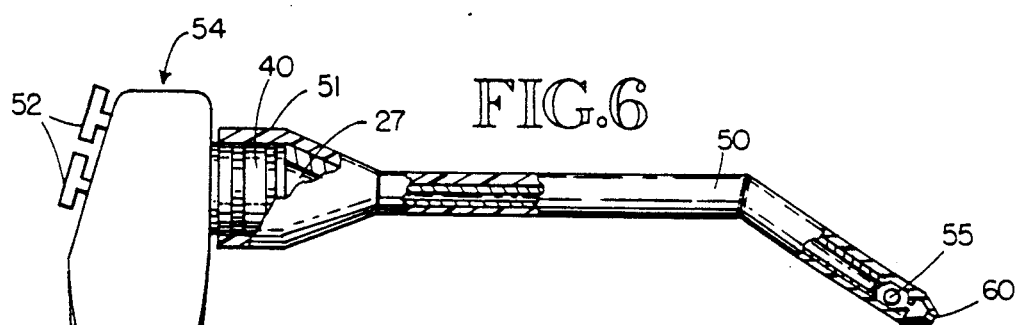
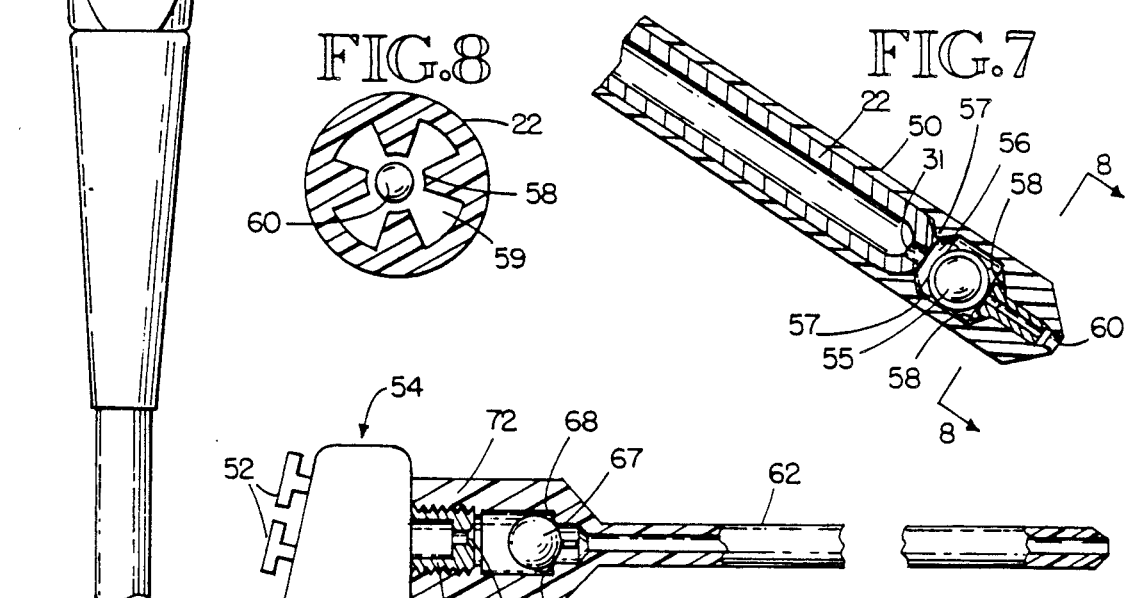
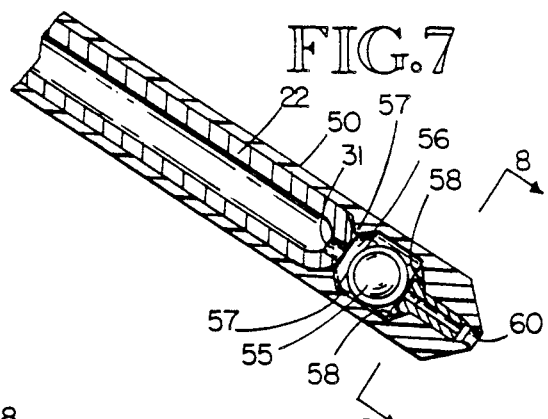
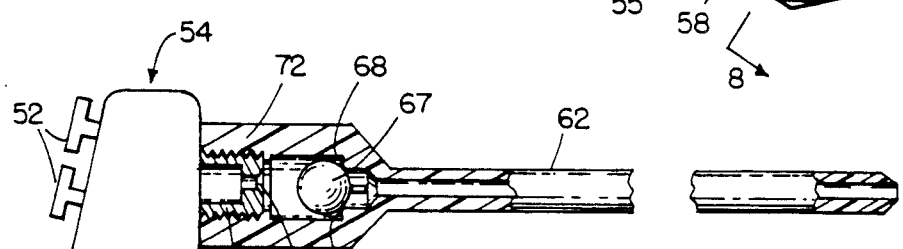
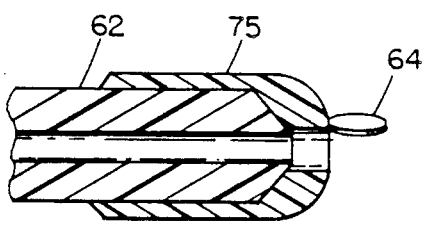
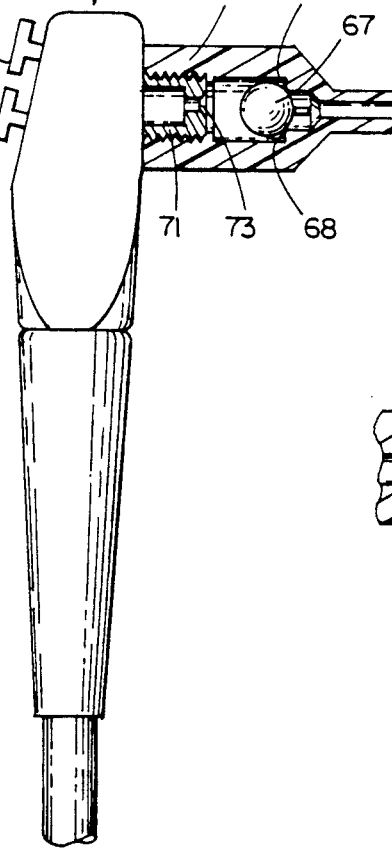

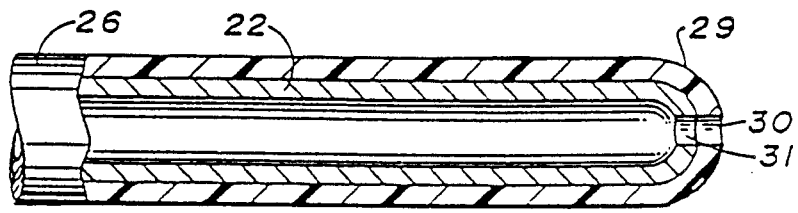
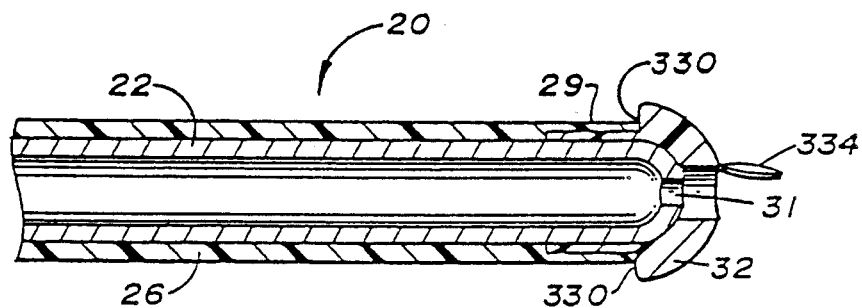
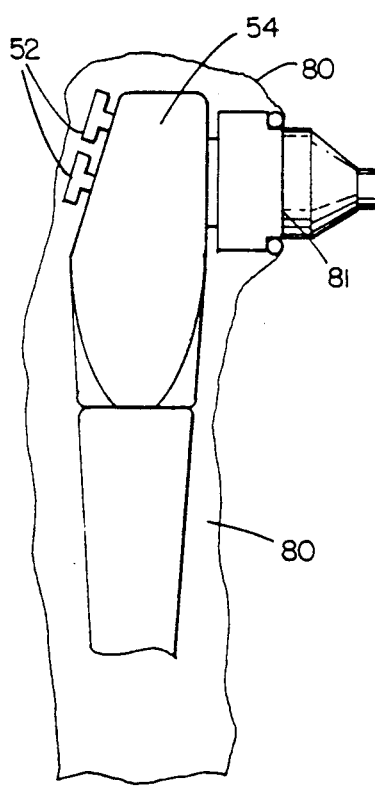
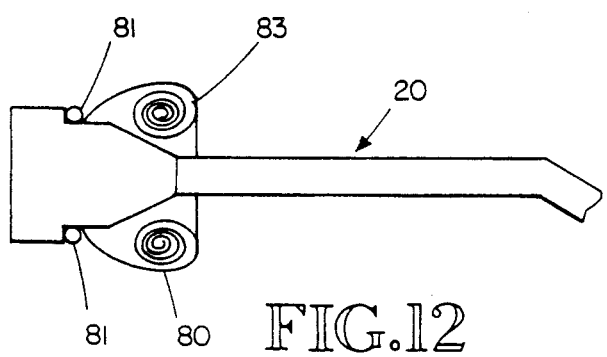

DENTAL SYRINGE SAFETY SHEATH APPARATUS

This is a continuation-in-part of copending application serial no. 118,170, filed on Nov. 9, 1987, now U.S. Pat. No. 4,859,182.

TECHNICAL FIELD

This invention relates to a dental syringe safety sheath apparatus adapted to minimize residual cross-contamination between patients. More specifically, the present invention relates to a disposable safety sheath which may be placed over the beak of a dental syringe used to apply a fluid to the inside of a patient's mouth.

BACKGROUND ART

The problem of residual cross-contamination between patients is of serious concern to the public and dental profession. This problem has received considerable attention due to the publicity of many known illnesses and diseases which may be communicated by the transfer of infected body fluids between patients. A dental syringe is often used to apply a suction or fluid, such as water or air, to the inside of a patient's mouth. Where a fluid is dispensed, the syringe is connected to a pressurized delivery system. In some dental syringe systems, an optional draw-back apparatus may be used with the delivery system. When the application of a liquid ceases, the draw-back apparatus produces a partial vacuum within the delivery lines, syringe and beak. The partial vacuum draws the liquid located within the syringe back into the delivery system, removing the liquid from the beak of the syringe. The draw-back apparatus prevents the leaking or dripping of liquid from the discharge orifice of the beak when the syringe is not used. Unfortunately, when the syringe is released from dispensing the liquid, the draw-back apparatus may suck contaminants, such as germs, blood, or saliva, from within the patient's mouth into the syringe or delivery system. These contaminants remain within the syringe or delivery system until liquid is subsequently dispensed, possibly into another patient's mouth.

Devices using sanitary covers have been designed in an effort to reduce the occurrence of injuries caused by dental hardware.

Curry (U.S. Pat. No. 1,485,963) discloses a disposable cover for a dental handpiece. The cover protects the handpiece from contacting the hand of the user or the mouth of the patient.

Fehrman (U.S. Pat. No. 2,655,725) discloses a grinding implement for use with small animals, particularly chinchillas, having a readily adjustable guard for the rotary burr to protect the mouth of the animal against injury.

Ikse (U.S. Pat. No. 2,696,669) discloses a device for supplying liquid during dental operations. Ikse ('669) teaches that the nozzle may be interchangeable.

Hawk (U.S. Pat. No. 4,286,950) discloses a removable cover for a dental handpiece, to protect the tool and enclose it when not in use.

These disclosures are believed to illustrate the general scope of the prior art in this area of dental technology. The applicant submits that these disclosures taken alone or together do not teach the concepts embodied in this invention.

DISCLOSURE OF INVENTION

It is the general object of the present invention to provide an apparatus which helps reduce residual cross-contamination between dental patients.

A further object is to provide an apparatus to cover and protect the beak of a dental syringe.

A still further object is to provide an apparatus which substantially prevents contaminants from being drawn through the discharge orifice into the beak of a syringe.

Another object is to provide an apparatus which is removable and disposable after use with each patient, thereby minimizing the need to sterilize the beak of the syringe after each use, although, periodic sterilization is advisable.

Another object of the invention is to provide a sheath that can be readily engaged with, and disengaged from, the beak of a dental syringe.

Another object of the invention is to provide a plastic, relatively stiff cap-type cover or sheath to protect the syringe, and enclose the beak's discharge orifice when fluid is not being discharged.

The present invention is a dental syringe safety sheath apparatus which acts as a protective cover for those portions of a beak of a dental syringe which will be used near or be inserted into a patient's mouth. The safety sheath apparatus provides a substantially sterile outer-covering for the beak and may be disposable after use with each dental patient.

The safety sheath apparatus has a sheath means, cover, or sleeve into which the beak of a dental syringe may be inserted. The sheath means is a generally elongated tube or cylinder adapted to substantially fit over and cover the beak of a dental syringe from the syringe handpiece to the beak's discharge orifice. The sheath is appropriately dimensioned to allow for proper, secure fitting on the beak and for easy removal. The sheath means is removably attached to the beak and is preferably form fitted to the shape of the dental beak. Where the beak has a defined axis, the sheath means is positioned coaxially with the axis of the beak. The sheath means has an open-end and a terminal-end. An opening in the open-end is sufficiently large to allow for the insertion of the beak into the sheath means. The terminal-end has an aperture, located near the discharge orifice of the beak, which allows fluid to be dispensed from the beak and sheath means into a dental patient's mouth.

A tip may be used independently or with the sheath means. The tip is removably attached to the terminal-end of the sheath means. Alternatively, the tip is an integral part of the terminal end of the sheath means. The tip covers the discharge orifice of the beak. When used together, the tip and sheath means provide a substantially sterile outer-covering for the beak and discharge orifice.

The tip has a small, movable valve means positioned near the aperture of the sheath means, coincidently with the discharge orifice of the beak. When open, the valve means allows a fluid to be dispensed from the beak and tip. The valve means closes to cover the aperture when the syringe is not being used. The purpose of the valve means is to close or cover the aperture when the fluid is no longer being dispensed, thereby, substantially preventing contaminants, such as the patient's body fluids, from entering or being drawn into the beak through the discharge orifice.

The valve means may be a flap-valve, hinged to the tip and made of material wherein the natural flexible properties of the material allow the flap-valve to be at least partially open when the pressure within the beak exceeds atmospheric pressure and the fluid is forced outward from the discharge orifice. The resiliency of the flexible material urges the flap-valve to be at least partially closed when the pressure within the beak approaches atmospheric pressure and the fluid no longer is forced outward from the discharge orifice. Alternative valve systems may also be used if the same effect is substantially achieved.

The sheath of this invention may extend over the enlarged portion of beak having internal threads for attachment to the base of the dental syringe to provide more complete coverage of the instrument.

Another embodiment of this invention utilizes a replaceable beak structure in place of the metal beak normally found in a dental syringe. Desirably, this replacement beak has an internal valve mechanism to prevent aspiration of the fluids back into the syringe. The structure may also be provided with an external valving mechanism as described above.

A drape or sleeve made of a thin flexible material may be provided to cover the entire dental syringe extending backwardly from the sheath over the body of the syringe. A flexible or flexible and stretchable material may be used for this purpose to completely enclose the syringe device.

Replacement of the sheath and tip with a new sheath and tip after use with each patent greatly reduces the possibility of residual cross-contamination of body fluids between dental patients. Although periodic sterilization of the beak of the syringe may still be advisable for absolute safety, the need for sterilization is greatly reduced.

An alternative embodiment of the present invention encompasses a small, movable valve means which is integrally or removably attached to a disposable beak. In such an embodiment, the valve means is located coincidently with the discharge orifice of the beak and similarly functions as described above.

BRIEF DESCRIPTION OF DRAWINGS

FIG. 1 is a perspective view of the preferred embodiment of the DENTAL SYRINGE SAFETY SHEATH APPARATUS as made in accordance with this disclosure.

FIG. 2 is a partial, cross-sectional, side elevational view of the apparatus shown in FIG. 1 as applied to a dental syringe.

FIG. 2a is an enlargement of the cross-sectional portion of the apparatus as applied to a dental syringe as shown in FIG. 2.

FIG. 3 is a partial, perspective view of a second embodiment of the present invention.

FIG. 4 is a partial, perspective view of a third embodiment of the present invention.

FIG. 5 is a partial, cross-sectional, side elevational view of a fourth embodiment of the present invention as applied to a dental syringe.

FIG. 5a is an enlargement of FIG. 5 to point out the elements of the fourth embodiment with greater particularity.

FIG. 6 is a side elevational view partly broken away showing a second embodiment of the sheath structure.

FIG. 7 is an enlarged cross sectional view of the tip of the device shown in FIG. 6.

FIG. 8 is a cross sectional view taken along lines 8—8 of FIG. 7.

FIG. 9 is a side elevational view of another embodiment of the invention partly in section showing the valve mechanism included in the replaceable beak structure.

FIG. 10 is a further tip embodiment.

FIG. 11 is a partial side elevational view showing the drape mechanism encompassing the syringe body.

FIG. 12 is a side elevational view of part of the apparatus shown in FIG. 11 showing the drape mechanism rolled in a suitable configuration for shipment.

BEST MODE FOR CARRYING OUT THE INVENTION

Referring to the drawings and particularly to FIGS. 1-4, wherein like numerals indicate like parts, the dental syringe safety sheath apparatus 20 comprises a sheath means 26 for sheathing beak 22 of a dental syringe 24. The sheath means 26 may take the form of a sheath, cover, or sleeve into which beak 22 may be inserted.

Sheath means 26 may be held onto beak 22 and syringe 24 by any conventional means which allows relatively easy placement and removal. Sheath means 26 should not be so loose when attached to beak 22 as to cause a danger of falling off beak 22 into the patient's mouth. Sheath means 26 is preferably a generally elongated cylinder, form fitted to the shape of beak 22, and adapted to substantially fit over and cover beak 22 from handpiece 27 to discharge orifice 31. A close fitting between sheath means 26 and beak 22 also minimizes the amount of contaminants which might become entrapped therebetween.

Sheath means 26 has an open-end 28 and a terminal-end 29. Terminal-end 29 has an aperture 30 located coincident or near the discharge orifice 31 of beak 22. In FIG. 3 the aperture is indicated by a cross-slit 130. Cross-slit 130 comprises a single or double incision through sheath means 26. A double incision forming an x-shape is shown. In FIG. 4 the aperture is indicated by an opening 230 which is covered by a hinged valve means 234. Sheath means 26 is shown in FIG. 5 as having an aperture 330 into which a tip 32 is inserted. Tip 32 is juxtaposed between terminal-end 29 of sheath means 26 and beak 22 near discharge orifice 31. Apertures 30, 130, 230 and 330 enable the fluid being discharged from dental syringe 24 to pass into the patient's mouth without excessive pressure being built up between beak 22 and sheath means 26.

These embodiments may incorporate the use of tip 32 and/or a valve means wherein apertures 30, 130, 230 or 330 allow a fluid to be dispensed from beak 22, but prevent contaminants from entering into discharge orifice 31 when application of the fluid ceases. The valve means may comprise a flap-valve which is only open when the pressure within beak 22 exceeds atmospheric pressure and the fluid is forced outward from discharge orifice 31.

The valve means and sheath means 26 may be made of material wherein the natural flexible action of the material allows the valve means to open when fluid is forced outward from beak 22, and close when the discharge of fluid ceases.

As shown in FIG. 5, tip 32 may comprise a separate device, having valve means 334 incorporated therein. Tip 32 attaches or snaps onto terminal-end 29 of sheath 26. Alternatively, valve means 134 and 234 may be formed as an integral part of sheath means 26 as respectively shown in FIG. 3 and FIG. 4. In FIG. 3, the valve means comprises the remaining flaps 134 which were formed by cross-slit 130. In FIG. 4, the valve means comprises the remaining flap 234 which is formed by a semicircular incision creating aperture or opening 230. Valve means 234 and 334 comprising a flap-valve are shown in FIG. 4 and FIG. 5 respectively. Valve means 234 is shown closed in FIG. 4. Valve means 334 is shown open in FIG. 5.

For a more complete coverage of the beak mechanism of this apparatus the embodiment shown in FIG. 6 is provided to encompass the knurled region 29 of beak 22. The sheath 50 has an enlarged portion 51 which snugly encases the tapered handpiece 27 and knurled region 40. Also shown in this embodiment is an internal ball-type valve mechanism shown best in FIG. 7 which includes a ball 55 held within chamber 56 by retainer 57. Since the sheath 50 is made of an elastomeric material, ball 55 may be inserted by thrusting it axially into the interior of sheath 50 and snapping it past retainer 57 into chamber 56. The ball may then move from one end to the other of chamber 56 encountering at one end the embossments 58 which permits flow of water or air around the embossments 58 through channels 59 as is best seen in FIG. 8. Whenever back flow occurs, the ball immediately travels against the exposed end of beak 22 at aperture 31 and seals there against preventing back flow. Alternatively, the device shown in FIG. 6 may have any of the tip structures shown in FIGS. 2, 3, 4, 5, and 10.

In the event a replaceable beak structure, as opposed to a covering, for the beak is desired, the apparatus shown in FIG. 9 may be utilized. The threaded outlet 71 of handpiece 54 is adapted to receive a female threaded portion 72 of the replaceable beak structure. As desired, a ball valve device may be incorporated within the structure as is shown in FIG. 9. Here ball 67 is adapted to seat against and seal aperture 73 preventing back flow of fluids into handpiece 54. The forward motion of the ball 67 when fluid flow occurs is arrested at embossment 68 preventing further movement of the ball yet permitting flow of fluid therearound. Depressing valve controls 52 permits selected flow of air or water through the handpiece.

In FIG. 10 a slide-on type end valve structure is shown which may be used with any of the previously described devices, as desired. An outer sheath 75 is adapted to slide upon for example beak 62 and provides additional valving action in the event of aspiration of water by closure of flap valve 64. This device may be used singly or in combination with other of the valve mechanisms described above.

Any of the sheaths or replaceable beaks described herein may also be equipped with a drape or flexible sleeve which may be unrolled from the beak area backwardly over the body of the syringe to fully encase the syringe in a disposable cover. The cover may be a latex rubber type material which is stretchable and tightly encases the handpiece or may be a drape of non extendible elastomeric film which merely drapes over the syringe body. The device shown in FIG. 11 shows drape 80 being extended over the top of syringe body 54 and downwardly so that the entire body of the syringe is covered. Drape 80 is attached at drape roll 81 to syringe cover sheath 20 at roll anchor 81. In FIG. 12 the sheath before attachment is shown with the stowed sleeve or drape 80 shown rolled up in roll 83 prior to installation. Once beak 20 is installed, the drape or sleeve may be rolled backwardly over the top of syringe body 54 to fully encompass the syringe. Access to valve controls 52 is available by merely depressing valves 52 through the drape material.

In compliance with the statute, the invention has been described in language generally specific to structural features. Since the means and construction herein disclosed comprise the preferred form of putting the invention into effect, it is to be understood the invention is not limited to the specific features shown herein. The invention is, therefore, claimed in any of its forms or modifications within the legitimate and valid scope of the appended claims, appropriately interpreted in accordance with the doctrine of equivalents.

INDUSTRIAL APPLICABILITY

This invention is particularly adapted for use by dental professionals on dental syringe equipment to minimize residual cross-contamination between patients. This invention comprises a disposable sheath which covers the beak of a conventional dental syringe. A tip may be provided with a valve means to allow for disbursement of a fluid from the beak into the patient's mouth, but prevent contaminants from being drawn into the syringe beak through the discharge orifice when the syringe no longer dispenses fluid.

I claim:

1. An apparatus comprising a disposable beak for a dental syringe, said beak having a syringe body engaging-end and a terminal-end, said syringe body engaging end having means to engage said syringe thereon in a fluid tight engagement and having a back flow preventing valve therein, said terminal-end having an aperture to allow a fluid to be dispensed therefrom.

2. The apparatus of claim 1, wherein said beak further includes a closure valve at said terminal-end to prevent back flow of fluids into said beak.

3. The apparatus of claim 1, wherein said beak means is disposable after use with a dental patient.

4. The apparatus of claim 1, further comprising a tip, said tip being located at said terminal-end of said beak, said tip providing a substantially sterile outer-covering for said beak and said aperture, valve means allowing said fluid to be dispensed from said beak and said tip while substantially preventing contaminants from entering or being drawn into said beak through said aperture.

5. The apparatus of claim 4, wherein said tip is removably attached to said beak.

6. The apparatus of claim 4, wherein said valve means is at least partially opened when the pressure within said beak, which forces said fluid outward from said aperture, exceeds atmospheric pressure, said valve means being at least partially closed when said pressure within said beak approaches atmospheric pressure.

7. The apparatus of claim 1 and drape means extendable rearwardly over said dental syringe body.

8. The apparatus of claim 4, wherein said valve means comprises a flexible flap-valve, said flap-valve being hinged to said tip, said flap-valve being made of a material wherein the natural flexible properties of said material allow said flap-valve to at least partially open when said fluid is forced outward from said discharge orifice, and to at least partially close when said fluid is not forced outward from said aperture.

9. An apparatus comprising a sheath adapted to cover the entire outer surface of a dental syringe beak, said sheath having a ball valve means adjacent a discharge orifice, said ball valve allowing a fluid to be dispensed from said discharge orifice and tip and substantially preventing contaminants from entering or being drawn into said dental syringe through said discharge orifice.

10. The apparatus of claim 9, wherein said tip is removably attached to said dental syringe.

11. The apparatus of claim 9, wherein said tip is an integral part of a beak of said dental syringe.

12. The apparatus of claim 11, wherein said beak is disposable after use with a dental patient.

13. The apparatus of claim 9, wherein said valve means is at least partially open when said pressure within said dental syringe, which forces said fluid outward from said discharge orifice, exceeds atmospheric pressure, said valve means being at least partially closed when said pressure within said dental syringe approaches atmospheric pressure.

14. The apparatus of claim 9, wherein said valve means comprises a flexible flap-valve, said flap-valve being hinged to said tip, said flap-valve being made of a material wherein the natural flexible properties of said material allow said flap-valve to at least partially open when said fluid is forced outward from said discharge orifice, and to at least partially close when said fluid is not forced outward from said discharge orifice.

* * * * *